United States Patent [19]

Janoski et al.

[11] Patent Number: 5,071,992

[45] Date of Patent: Dec. 10, 1991

[54] PROCESS FOR PREPARATION OF AROMATIC THIOL ESTERS

[75] Inventors: Helen L. Janoski, St. Peters; Mitchell J. Pulwer, St. Louis, both of Mo.

[73] Assignee: Monsanto Company, St. Louis, Mo.

[21] Appl. No.: 623,821

[22] Filed: Dec. 7, 1990

[51] Int. Cl.$^5$ .................. C07C 327/26; C07D 213/80
[52] U.S. Cl. ..................................... 546/315; 546/314; 558/251; 558/257
[58] Field of Search ................ 546/314, 315; 558/251, 558/257

[56] References Cited

U.S. PATENT DOCUMENTS 4,692,184 9/1987 Lee .......................... 71/94

Primary Examiner—Richard L. Raymond
Attorney, Agent, or Firm—Grace L. Bonner; Howard C. Stanley

[57] ABSTRACT

A process for producing an aromatic thiolester by mixing an alkyl or aryl thiol with an alkali metal hydroxide aqueous solution and, in the presence of a phase transfer catalyst, reacting it with an aromatic acid halide. Diacid halides may be used to produce bisthiol esters.

20 Claims, No Drawings

PROCESS FOR PREPARATION OF AROMATIC THIOL ESTERS

FIELD OF THE INVENTION

The present invention provides a process for the preparation of aromatic thiol esters, including bisthiol esters.

BACKGROUND OF THE INVENTION

It is well known that the esterification of acid chlorides and alcohols can be carried out in the presence of a base, such as sodium or potassium hydroxide, in aqueous solution. Even when a two-phase system is necessary due to solubility limitations, the reaction will proceed readily. However, when a thiol ester is desired and thus a mercaptan is used instead of an alcohol, the reaction does not proceed under the same conditions. Different and less effective anhydrous reaction conditions have been used. For example, U.S. Pat. No. 4,692,184 (Lee, Sept. 8, 1987) discloses a method of making pyridine carbothioates in Examples 141 and 146–149, but the only yield reported is 17.21%. The pyridine carboxyl chloride was mixed with the desired alkyl thiol and tetrahydrofuran in the presence of potassium tert-butoxide, and the resulting pyridine carbothioate was isolated. Therefore, there remains a need in the art for an improved process having improved yields, and preferably requiring less expensive solvents and/or less expensive bases.

SUMMARY OF THE INVENTION

The present invention provides a process for the preparation of an aromatic thiol ester comprising the steps of mixing an alkyl or aryl thiol with an aqueous solution of an alkali metal hydroxide; and reacting the ion thus formed, in the presence of a phase transfer catalyst (PTC), with an aromatic acid halide in an organic solvent. This is illustrated by the following:

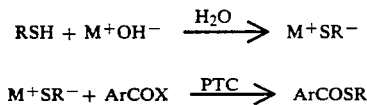

An advantage of the process of the present invention is that essentially all of the desired thiol ester will be present in the organic phase of the reaction mixture. The aqueous layer, containing the phase transfer catalyst and any excess alkyl thiol or alkali metal hydroxide, may be easily separated and then refortified for subsequent reactions. Thus the amount of waste from the reaction may be minimized.

DETAILED DESCRIPTION OF THE INVENTION

Most phase transfer catalysts will be operable in the present invention process. It is preferred that the catalyst be a quaternary ammonium salt, for example, benzyl triethyl ammonium hydroxide, tetra-n-propyl ammonium chloride, tetra-n-butyl ammonium chloride, tetrapentyl ammonium chloride, tris(dioxa-3,6-heptyl)amine, methyl tributyl ammonium hydroxide, or tricaprylyl methyl ammonium chloride. The catalysts may be used in liquid or solid form.

The organic solvent may be any solvent which is capable of dissolving the aromatic acid halide and which does not substantially interfere with the reaction. It is preferred that the solvent be immiscible with water. Examples include, but are not limited to, methylene chloride, cyclohexane, methylcyclohexane, and toluene. Mixtures of solvents, for example Aromatic 150 may also be used. The optimum solvent may be selected by routine experimentation based on the desired product and the catalyst chosen.

The temperature under which the reaction may be carried out may range from about 5° C. to the boiling point of the solvent chosen, preferably between about 10° and about 50° C., and more preferably at about 25° C. Ambient pressure is preferred, but not required. The reaction will proceed to substantial completion within about one to about twelve hours, depending on the temperature chosen. At the preferred temperature, a minimum reaction time of about 2½ hours may be needed to achieve greater than 90 percent completion.

The alkali metal hydroxide is preferably sodium or potassium hydroxide. It is used as an aqueous solution. Any concentration may be used, but it is preferred to use from about 10 to about 20 percent by weight in water.

Examples of alkyl thiols which may be used in the process of the present invention include methane thiol, ethane thiol, propane thiol, or butane thiol. Aryl thiols may also be used, such as benzyl mercaptan. Some substituted alkyl or aryl thiols may be used if the substituted group or groups do not appreciably interfere with the reaction steps.

The aromatic acid halide is selected according to the desired product. It may be a benzene derivative, for example, benzoyl chloride, or it may be a hetero aromatic derivative, such as pyridine carbonyl halide. It may contain more than one acid halide group, as in a diacid halide. A preferred pyridine carbonyl halide is 2-difluoromethyl-4-(2-methylpropyl)-6-trifluoromethyl-3,5-pyridine dicarbonyl chloride. Thiol esters of this pyridine are disclosed as useful as herbicides in U.S. Pat. No. 4,692,184, incorporated herein by reference. One such bisthiol ester is dimethyl 2-difluoromethyl-4-(2-methylpropyl)-6-trifluoromethyl-3,5-pyridine dicarbothioate, hereinafter referred to by the herbicide common name, dithiopyr.

The molar ratio of reactants is not critical; however, it is preferred that the alkyl or aryl thiol be present in molar excess over the aromatic acid halide it is to be reacted with. More preferably it is present at about a 30 percent molar excess. The base must be present in at least a stoichiometric amount for each esterification, that is, when one mole of a monoacid halide is reacted with one mole of an alkyl thiol, at least one mole of alkali metal hydroxide must be present. It is preferred that an excess from about 5 to about 30 percent be used, and more preferably, a 10 percent excess.

The phase transfer catalyst may be first dissolved in the aqueous mixture of the alkyl or aryl thiol and the alkali metal hydroxide, or it may be added to the reaction mixture with the aromatic acid halide or organic solvent. The organic solvent and aromatic acid halide be added to the aqueous mixture, or the aqueous mixture may be added to the organic phase. The rate of addition would be adjusted depending of the order chosen.

The desired aromatic thiol ester may be isolated from the reaction mixture by conventional methods. For example the aqueous and organic phases may be separated and the organic solvent removed under reduced pressure to provide the product.

The following examples are illustrative of the present invention, but in no way are meant to limit its application to the specific reactants or conditions described. As used therein, A336 refers to tricaprylyl methyl ammonium chloride; Tris refers to tris(dioxa-3,6-heptyl)amine; BTE refers to benzyl triethyl ammonium hydroxide; TP refers to tetrapropyl ammonium chloride; TB refers to tetra-n-butyl ammonium chloride; MTBA refers to methyl tributyl ammonium hydroxide; and TPENT refers to tetrapentyl ammonium chloride. Mecyclohexane means methylcyclohexane.

EXAMPLE 1

Preparation of Dithiopyr

Methane thiol, 0.5 g, was added to 4.3 g 10 percent sodium hydroxide aqueous solution with stirring at 25° C. To this was added 0.1 g A336. 2-difluoromethyl-4-(2-methylpropyl)-6-trifluoromethyl-3, 5-pyridine dicarbonyl chloride, 2 g, prepared as in Example 141 of U S. Pat. No. 4,692,184, dissolved in 2 g methylene chloride, was added. The resulting mixture, having a 20 percent excess of alkyl thiol and a 20 percent excess of base, was vigorously stirred for 12 hours at 25° C. The organic layer was separated, washed with water, and dried over magnesium sulfate. The solvent was removed under reduced pressure leaving an oil that solidified on standing. The solid was assayed by nmr and found to be the desired product, dithiopyr. The yield was 100%.

The following examples were done following the general procedure of Example 1, varying the ratios, conditions, or catalyst as shown in Table 1. In Examples 13, 14, and 15, a 20 percent potassium hydroxide aqueous solution was used instead of a 10 percent sodium hydroxide solution.

TABLE 1

| Ex. No. | Solvent | Catalyst | Catalyst Charge | Excess Thiol | Excess Base | Temp. °C. | Time (hrs) | Percent Yield |
|---|---|---|---|---|---|---|---|---|
| 2 | cyclohexane | Tris | 1% | 10% | 10% | 25 | 7 | 54 |
| 3 | cyclohexane | BTE | 1% | 10% | 10% | 25 | 6.5 | 50 |
| 4 | cyclohexane | TP | 1% | 10% | 10% | 25 | 7 | 47 |
| 5 | cyclohexane | BTE | 2% | 10% | 10% | 25 | 5 | 57 |
| 6 | cyclohexane | TP | 2% | 10% | 10% | 25 | 5 | 63 |
| 7 | cyclohexane | TP | 4% | 10% | 10% | 25 | 4 | 58 |
| 8 | cyclohexane | TP | 5% | 30% | 30% | 25 | 1.5 | 84 |
| 9 | Mecyclohexane | TP | 5% | 30% | 30% | 25 | 2.5 | 99 |
| 10 | Mecyclohexane | TP | 5% | 30% | 30% | 25 | 2.5 | 99 |
| 11 | toluene | TB | 5% | 30% | 30% | 65 | 1.5 | 99 |
| 12 | cyclohexane | TB | 5% | 30% | 30% | 65 | 1.0 | 83 |
| 13 | aromatic 150 | TB | 5% | 30% | 30% | 25 | 1.5 | 97 |
| 14 | toluene | MTBA | 4% | 12% | 12% | 25 | 2.5 | 89 |
| 15 | toluene | TPENT | 1% | 12% | 12% | 25 | 2.5 | 87 |

EXAMPLE 16

Comparative Preparation of Dithiopyr

The process of Example 1 was followed except that no phase transfer catalyst was used, but a 100 percent excess of methane thiol and a 100 percent excess of sodium hydroxide were used. No dithiopyr was detected in the organic layer after the twelve hour reaction.

What is claimed is:

1. A process for the preparation of an aromatic thiol ester comprising the steps of a. mixing an alkyl or aryl thiol with an aqueous solution of an alkali metal hydroxide; and
   b. in the presence of a phase transfer catalyst, reacting the product of step a. with an aromatic acid halide in an organic solvent.

2. The process of claim 1 wherein said alkyl thiol is methane thiol, ethane thiol, propane thiol, or butane thiol.

3. The process of claim 2 wherein said alkyl thiol is methane thiol.

4. The process of claim 1 wherein said aryl thiol is benzyl mercaptan.

5. The process of claim 1 wherein steps a. and b. are carried out at temperatures between 5° C. and the boiling point of the organic solvent.

6. The process of claim 5 wherein steps a. and b. are carried out at temperatures between 10 and 50° C.

7. The process of claim 6 wherein steps a. and b. are carried out at about 25° C.

8. The process of claim 1 wherein said phase transfer catalyst is a quaternary ammonium salt.

9. The process of claim 8 wherein said quaternary ammonium salt is benzyl triethyl ammonium hydroxide, tetra-n-propyl ammonium chloride, tetra-butyl ammonium chloride, tetra-pentyl ammonium chloride, tris(dioxa-3,6-heptyl)amine, methyl tributyl ammonium hydroxide, or tricaprylyl methyl ammonium chloride.

10. The process of claim 1 wherein said alkali metal hydroxide is sodium hydroxide or potassium hydroxide.

11. The process of claim 10 wherein said alkali metal hydroxide is present in molar excess to said alkyl thiol.

12. The process of claim 1 wherein said alkyl or aryl thiol is present in molar excess to said aromatic acid chloride.

13. The process of claim 12 wherein said alkyl or aryl thiol is present in 1 to 200 percent molar excess to said aromatic acid chloride.

14. The process of claim 13 wherein said alkyl or aryl thiol is present in about 30 percent molar excess to said aromatic acid chloride.

15. The process of claim 1 wherein said organic solvent is methylene chloride, cyclohexane, methylcyclohexane, or toluene.

16. The process of claim 1 wherein said aromatic acid halide is a diacid halide and at least two molar equivalents of said alkyl thiol are present, thus forming an aromatic bisthiol ester.

17. The process of claim 16 wherein said aromatic acid halide is a 3,5-pyridine dicarbonyl chloride.

18. The process of claim 17 wherein said 3,5-pyridine dicarbonyl chloride is 2-difluoromethyl-4-(2-methylpropyl)-6-trifluoromethyl-3,5-pyridine dicarbonyl chloride.

19. A process for the production of dimethyl 2-difluoromethyl-4-(2-methylpropyl)-6- trifluoromethyl-3, 5-pyridine dicarbothioate comprising the steps
   a. mixing methane thiol with an aqueous solution of an alkali metal hydroxide; and
   b. in the presence of a phase transfer catalyst, reacting the product of step a. with 2-difluoromethyl-4-(2-methylpropyl)-6-trifluoromethyl-3,5-pyridine dicarbonyl chloride in an organic solvent.

20. The process of any of claims 1 to 19 wherein the reaction is carried to substantial completion and the desired thiol ester is thereafter isolated from the reaction mixture.

* * * * *